United States Patent [19]

Schoolman

[11] Patent Number: 4,483,562
[45] Date of Patent: Nov. 20, 1984

[54] LOCKING FLEXIBLE SHAFT DEVICE WITH LIVE DISTAL END ATTACHMENT

[76] Inventor: Arnold Schoolman, 8705 Catalina Dr., Prairie Village, Kans. 66207

[21] Appl. No.: 312,008

[22] Filed: Oct. 16, 1981

[51] Int. Cl.³ ................................................ B25J 1/02
[52] U.S. Cl. .................................. 294/19 R; 81/57.43; 81/177 F; 128/321; 294/104
[58] Field of Search .................. 294/19 R, 22, 99 R, 294/100, 104, 115, 111; 15/104.3 G; 81/57.27, 57.43, 177 F; 128/321; 464/72, 91, 99, 170, 171, 173, 176-178

[56] References Cited

U.S. PATENT DOCUMENTS

| | | | |
|---|---|---|---|
| 1,519,938 | 12/1924 | Smith | 294/104 X |
| 1,698,952 | 1/1929 | Hoover | 81/57.43 X |
| 1,990,686 | 2/1935 | Einhorn et al. | 294/111 X |
| 2,595,134 | 4/1952 | Gordon | 294/99 R |
| 3,203,285 | 8/1965 | Schmidt | 81/177 F |
| 3,399,584 | 9/1968 | Lewecki | 81/177 |
| 3,585,885 | 6/1971 | Carr | 81/177 F |
| 3,777,538 | 12/1973 | Weatherly et al. | 128/325 |
| 3,986,743 | 10/1976 | Bjurling et al. | 294/19 R |
| 4,033,618 | 7/1977 | Lamb | 294/19 R |
| 4,235,238 | 11/1980 | Ogui et al. | 128/335 |
| 4,253,697 | 3/1981 | Acosta | 294/115 |

FOREIGN PATENT DOCUMENTS

1171354 10/1957 Fed. Rep. of Germany.

Primary Examiner—Johnny D. Cherry
Attorney, Agent, or Firm—Litman, Gold & McMahon

[57] ABSTRACT

The device includes a shaft having a plurality of interengaging shaft members. A tension member extends through the shaft and is positional between two positions. When the tension member is in the first position thereof, the shaft members are capable of movement relative to one another allowing the shaft to be manipulable between a continuous range of positions. When the tension member is biased to the second position thereof, the shaft members are non-movably held together forming a rigid shaft of desired shape. An articulation member extends through the shaft and is connected to a live attachment which is retained on a distal end of the shaft. By manipulation of the articulation member at a proximal end of the shaft the live attachment is manipulated.

7 Claims, 8 Drawing Figures

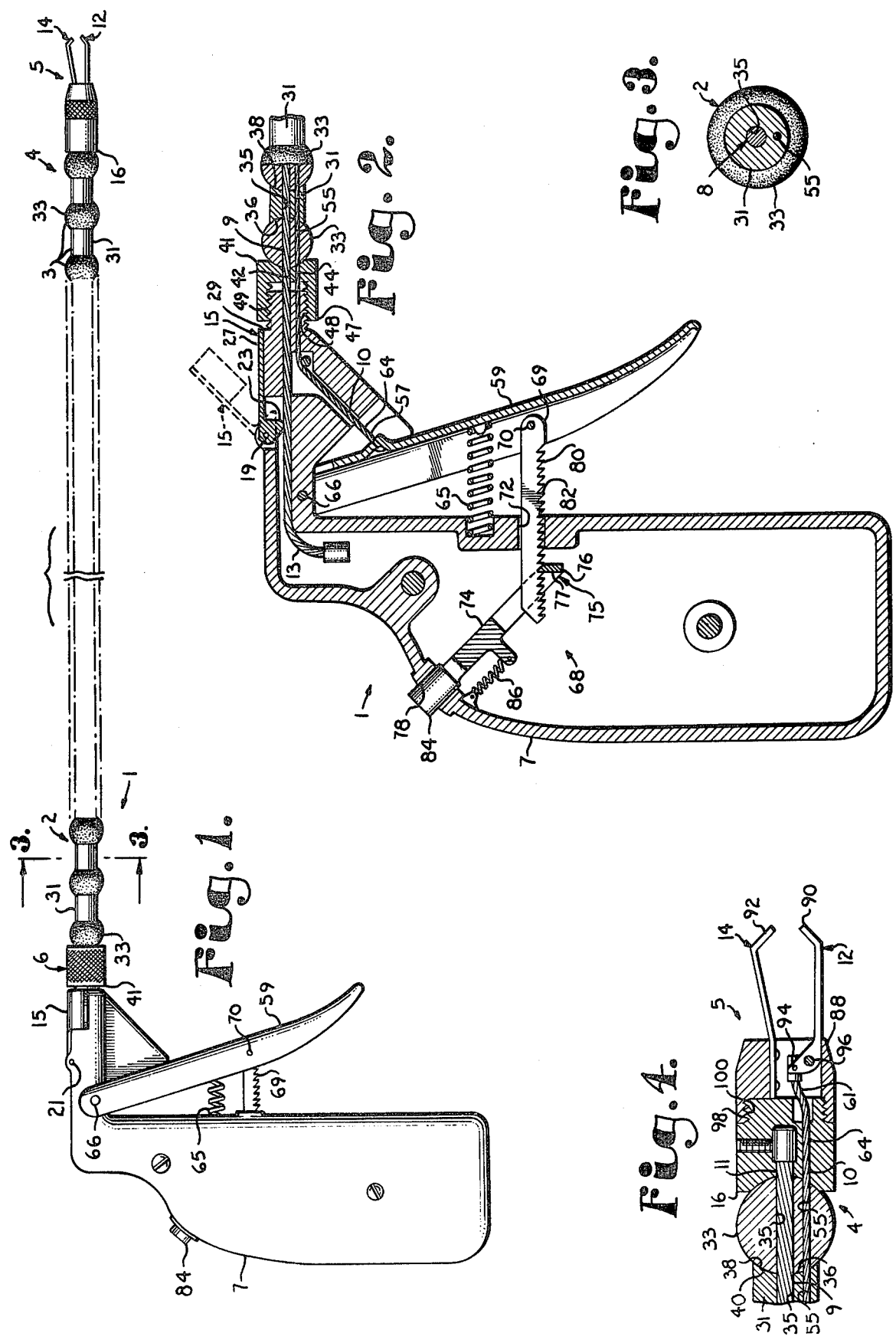

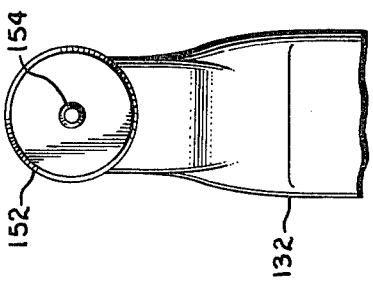
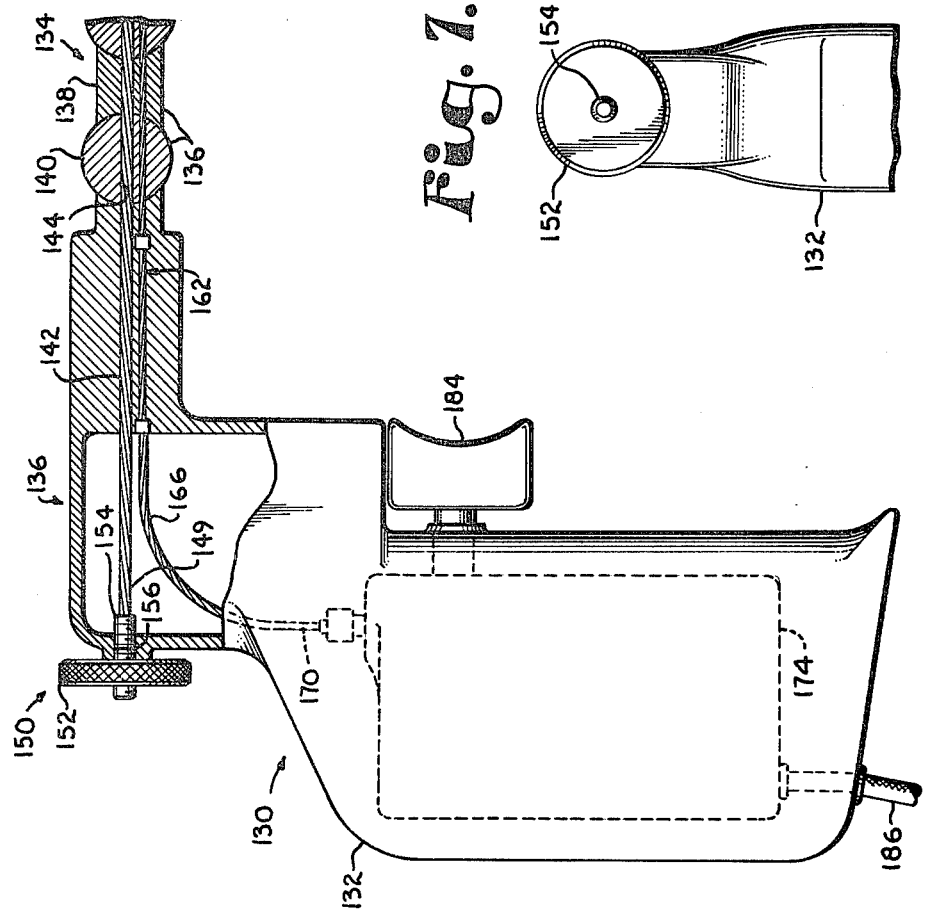
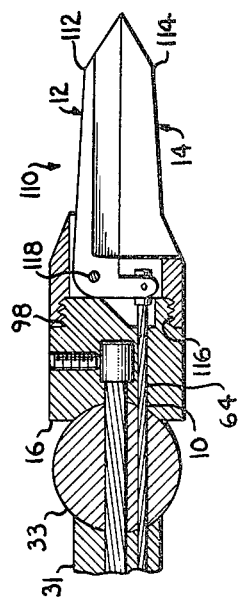
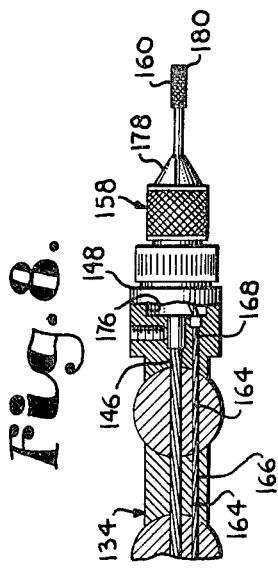

LOCKING FLEXIBLE SHAFT DEVICE WITH LIVE DISTAL END ATTACHMENT

BACKGROUND OF THE INVENTION

The present invention relates to a flexible shaft device having a tool attachment at one end thereof and in particular, to a flexible shaft which can be locked rigidly in a desired shape having a live tool attachment at a distal end thereof manipulable by a user of the device.

Often times it is necessary for an individual to have the use of a flexible shaft device which has a live attachment such as a pair of scissors or retaining clips on a distal end thereof with the shaft being capable of being manipulated to a desired shape to avoid obstructions in an area of work. An example of this is when, as during surgical operations, it is necessary for a surgeon to be able to retain certain items such as tissues or the like in a desired position while performing the surgery. In order to free the hands of the surgeon and those of any assistant, it is preferable to use such a shaft having a lockable clip which can be attached to the tissue to retain the tissue in a desired position. It is preferable that such a shaft be flexible which allows the shaft to be placed out of the way of the surgeon.

Another example of a need for such a device is where a worker, such as a mechanic or the like, needs to manipulate a work piece such as a socket or a screwdriver on a desired object, such as a bolt or screw, which object, for one reason or the other, is not readily accessible by his hands but is accessible by a flexible shaft having a suitable live work piece at an end thereof.

Prior examples of such devices have not included the ability to rigidly retain the flexible shaft in a desired shape for accomodating these objectives. This is especially important as it allows the user more freedom of movement than non-locking shafts which have a tendency to continually deviate from a desired shape during the use thereof.

OBJECTS OF THE INVENTION

Therefore, the objects of the present invention are: to provide a locking flexible shaft device with distal end attachment which is capable of assuming a continuous range of flexed shapes and being selectively and rigidly locked therein; to provide such a shaft for such a device which comprises a plurality of engaging members held together by a tensioning member, which tensioning member is positionable between a first position where the shaft members are free to move relative to one another and a second position where the shaft members are rigidly and non-movably held relative to one another in a combined desired shape; to further provide such a shaft which includes an articulation member which passes through the shaft members and which is attached at one end thereof to a live attachment retained at the distal end of the shaft and at the other end thereof to a manipulation means which allows a user of the device to manipulate the live attachment; to provide such a shaft which includes an articulation member thereof which reciprocates within the shaft members; to provide such a shaft which includes an articulation member thereof which rotates within the shaft members; to further provide for such a shaft, a plurality of suitable devices attachable to a distal end of the shaft for carrying on a plurality of desired work processes; and to provide such a locking flexible shaft device which is durable in use, easy to use, capable of a variety of uses and is extremely well adapted for the intended usage thereof.

Other objects and advantages of this invention will become apparent from the following description taken in connection with the accompanying drawings wherein are set forth, by way of illustration and example, certain embodiments of this invention.

SUMMARY OF THE INVENTION

The present invention comprises a locking flexible shaft device with live distal end attachment. The device includes a shaft having a plurality of engaging shaft members which have passing therethrough a tensioning member and an articulation member. The tensioning member is positionable between one of two positions. When the tensioning member is placed in the first position thereof, the shaft members are freely manipulable relative to one another such that the shaft can be manipulated into a desired shape. When the tensioning member is in the second position thereof, the wire through the shaft members is tightened which forces the individual shaft members into frictional contact with one another prohibiting the shaft members from movement relative to each other. When this occurs, the shaft rigidly assumes the desired shape.

The articulation member passes through the shaft members and is attachable at a first end thereof to a work device which is retained on a distal end of the shaft. A second end of the articulation member is attached to a manipulation means which allows a user of the flexible shaft to manipulate the live attachment. The live attachment can be of two types, either an attachment wherein a live member thereof reciprocates between one of two positions or where a live member thereof revolves or rotates about an axis usually concentric with an axis of the shaft. In order to reciprocate the attachment live member, the articulation member comprises a wire which reciprocates within the first flexible shaft. For rotation of the live member, a suitable electric motor is provided with the shaft to rotate the articulation member and therefor the live attachment. The live attachment can be a suitable work tool such as a pair of scissors, gripping clips, screwdriver blade, socket adapter or the like.

The drawings constitute a part of this specification and include exemplary embodiments of the present invention and illustrate various objects and features thereof.

BRIEF DESCRIPTION OF THE DRAWINGS

FIG. 1 is a side elevational view of a first embodiment of a locking flexible shaft device having a live attachment according to the present invention.

FIG. 2 is an enlarged cross-sectional view of a handle and part of a shaft of such a device.

FIG. 3 is an enlarged cross-sectional view of the shaft taken generally along line 3—3 in FIG. 1.

FIG. 4 is an enlarged fragmentary cross-sectional view of a distal end of the device shaft showing a first manipulable live attachment thereon.

FIG. 5 is an enlarged fragmentary, cross-sectional view of the device shaft distal end showing a second manipulable live attachment thereon.

FIG. 6 is a side elevational view of a handle and a portion of a shaft of a second embodiment of a locking flexible shaft device having a live attachment according to the present invention.

FIG. 7 is a front elevational view of the device as shown in FIG. 6.

FIG. 8 is an enlarged fragmentary, cross-sectional view of a distal end of the device as shown in FIG. 6 showing a manipulable live attachment attached thereto.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally refers to a locking flexible shaft device with live distal end attachment according to the present invention. As shown in FIG. 1, the device includes a shaft 2 comprising a plurality of engaging shaft members 3 and including at a shaft distal end 4 thereof, a live attachment 5 and at a proximal end 6 thereof, a suitable handle 7. The shaft further includes a tensioning member 8 and an articulation member 10.

The tensioning member 8, shown here as a wire 9, extends through the shaft members 3 and is attached at a first end 11 thereof to an end shaft member 16 which comprises the shaft distal end 4 and at a second end 13 thereof to the handle 7. The tensioning member 8 is positionable between two positions. When the tensioning member 8 is in a first position thereof, the shaft members 3 are freely movable relative to one another such that the shaft members 3 can assume a desired shape. When the tensioning member 8 is in a second position thereof, the shaft members 3 are rigidly and non-movably held together such that the shaft members 3 are non-movably retained in the desired shape.

A tightening lever 15 engages the tensioning member 8 at the second end 13 thereof. The lever 15 is pivotable about pin 19 which is received in bores 21 in handle 7. The lever 15 includes a tang 23 which engages a surface of the tensioning member 8. When the lever 15 is rotated to a position shown in solid lines in FIG. 2, tang 23 is urged against the tensioning wire 9 biasing the wire 9 downwardly at the point of contact thereby increasing the tension within the wire. When the lever 15 is thusly positioned, the tensioning member 8 is positioned in its second position thereof where the shaft members 3 are securely held to one another. When the lever 15 is rotated about the pin axis upwardly as shown in dotted lines in FIG. 2, the tensioning member 8 is in the first position thereof such that tang 23 is biased out of engagement with wire 9, releasing tension in the wire 9 whereby the shaft members 3 are freely movable relative to each other. When the lever 15 is rotated downwardly, a top surface 27 of the lever 15 and a top surface 29 of the handle are substantially flush so as to not present irregularities which might obstruct movement relative to the handle 7.

The shaft members 3 include a plurality of alternating spacers 31 and spheres 33 each having a longitudinal axial bore 35 therethrough, through which is received the tensioning member 8. The spacers 31 include at both ends thereof, a generally hemispherical indentation 36 which mates with a surface of an associated sphere 33.

The spacers 31 and spheres 33 include mating surfaces, 38 and 40 respectively, which are preferably irregular and therefor have bumps thereon so as to provide a high degree of friction therebetween when the spacers and spheres 31 and 33 are biased into forceful engaging contact such as when the tensioning member 8 is biased to the second position thereof.

A tubular tension adjuster 41 is provided at the connection between the handle 7 and the shaft members 3 and has bores 42 and 44 therethrough for receipt of tensioning member 8 and articulation member 10. The tension adjuster 41 includes at a first end 47 thereof an enlarged threaded bore 48 which is received over a threaded portion 49 of handle 7. The tension adjuster 41 telescopes longitudinally relative to handle 7 upon rotation therewith to adjust the tension in wire 9 when the wire 9 is in the second position thereof as when the lever 15 is positioned as shown in solid lines in FIG. 2. This is to assure that the proper amount of tension exists in the tensioning wire 9 so that the shaft 1 remains substantially rigid.

The articulation member 10 passes through the shaft members 3 and is received within bores 55 therein. The articulation member 10 is attached at a first end 57 thereof to a manipulator handle or trigger 59 and at a second end 61 thereof to the movable member 12 of live attachment 5. When the shaft 1 is retained in rigid shape the articulation member 10 is capable of manipulating the live attachment 5 to carry out a desired work process. The articulation member 10 can either reciprocate within shaft member bores 55 or can rotate therein.

In the first embodiment of the present invention as shown in FIGS. 1 through 5, the articulation member 10 comprises a wire 64 of suitable tensile strength and which reciprocates within the shaft members 3 to perform the desired work process. In this embodiment, the trigger 59 is pivotally attached to the shaft handle 7 by means of pivot pin 66 or the like. The wire 64 is attached to the trigger 59 such that when the trigger 59 is biased toward handle 7 from a first outer position thereof, as by being squeezed by a hand of the user, the wire 64 is pulled through the shaft member 3 in a direction toward the handle 7. A suitable spring 65 is provided to bias the trigger 59 away from handle 7 upon releasing the trigger 59 such that the trigger 59 will return to the first position biasing the wire 64 in a direction toward the live attachment 5.

A suitable locking mechanism 68 is provided to retain the trigger 59 in an inward position thereof. As shown in FIG. 2, the locking mechanism 68 includes a finger 69 which is pivotally attached to the trigger 59 at pin 70 and which is received within a slot 72 in handle 7. Also included is a stop mechanism 74 which extends into handle 7 at a position opposed to that of slot 72 which stop mechanism 74 includes at an inner end 75 thereof, a tab 76. As shown, the stop mechanism 74 reciprocates within a second slot 78 in handle 7.

As shown, the finger 69 includes a series of serrations or ridges 80 which include a first surface 82 thereof which mates with a surface 77 of the stop mechanism tap 76 to restrain the trigger 59 from movement away from handle 7. It is seen that the position of trigger 59 relative to handle 7 is maintained by the combined cooperation of spring 65 which functions to bias trigger 59 away from handle 7 and which forces a serration first surface 82 into forceful contact with the stop mechanism tab surface 77. As such, the position of the live attachment movable member 12 remains constant relative to the live attachment stationary member 14.

The stop mechanism 74 may be released by applying pressure inwardly on an exposed end or button 84 thereof which biases the tang 76 away from contact with the finger 69. When the stop mechanism 74 is biased inwardly as such, the trigger 59 is allowed to freely move relative to handle 7. A tension spring 86 is provided engaging handle 7 and stop mechanism 74 which continually exerts a force on the stop mechanism 74 in a direction outwardly of slot 78 which acts to keep the tab 76 in forceful contact with the finger serration first surfaces 82. It is seen that the mating surfaces 82 and 77 of the finger 69 and stop mechanism tang 76, respectively, are oriented as to be substantially normal to a line of motion of finger 69 as it reciprocates within slot 72 thereby preventing inadvertent releasing of the stop mechanism.

As shown in FIG. 4, the live attachment 5 can be a surgical clip 88 having a movable clip member 90 and a stationary clip member 92. As seen in FIG. 4, the movable clip 90 is attached to the articulation member 10 by a suitable fastener such as a retaining pin 94 and is pivotally connected to the surgical clip 88 by means of pivot pin 96. The clip is suitably retained to the end shaft member 16. As shown herein, the end shaft member 16 includes an outer threaded portion 98 over which is threadably received a threaded bore 100 of clip 88.

As shown in FIG. 5, the live attachment 5 can be a pair of scissors or cutters 110 which is selectively interchangeable with clips 88. The scissors 110 comprise a movable scissor member 112 and a stationary scissor member 114. The scissors 110 include a threaded bore 116 which is threadably received on the shaft end member threaded portion 98.

The scissors movable member 112 is mounted on pin 118 so as to be pivotal relative to the scissors member 114.

In use, the shaft 2 of the device 1 is manipulated into a desired shape. In order to do so, the tensioning member 8 must be in the first, untensioned, position thereof such that the shaft members 3 are free to move relative to each other. Preferably, prior to manipulation of the shaft 2, the desired live attachment member 5 is operably attached thereto. After the desired shape of the shaft 2 has been achieved, the tensioning member 8 is biased to a second, tensed, position by moving lever 15 until it is substantially flush with handle 7. As mentioned, when the lever 15 is in this position, the shaft members 3 are forced into engaging frictional contact with each other and are thereby prohibited from movement relative to one another such that the shaft 2 rigidly retains the intended desired shape. If the tension in tension member 8 is either too great or too small, the tension adjuster 41 can be rotated relative to handle 7 which changes the effective length of the shaft 2 and therefore the tension in tensioning member 8 when biased to the second position thereof.

When the tensioning member 8 is in the second position thereof and the shaft 2 is rigidly retained in a desired shape, the live attachment movable member 12 can be manipulated by manipulating the trigger 59 such as by biasing the trigger 59 toward handle 7. It is seen that when the trigger 59 is biased toward the handle 7, the live attachment movable member 12 is activated. If the surgical clip 88 is installed on the shaft distal end 4, the clip movable member 90 is biased toward the clip stationary member 92 when the trigger 59 is biased toward handle 7 to retain a desired item therebetween. If the scissors member 110 is installed on the shaft member 16, the trigger 59 can be alternately biased toward and away from handle 7 by holding the stop mechanism 74 inwardly relative to handle 7. In doing so, the articulation member 10 reciprocates in bores 55 in shaft members 3 and causes scissors live member 112 to alternately be biased toward and away from the scissor stationary member 114 thereby affecting a scissoring motion.

The reference numeral 130 generally represents a second embodiment of a locking flexible shaft device with live distal end attachment according to the present invention as shown in FIGS. 6 through 8. The device 130 includes a handle 132 and a shaft 134 comprised of a plurality of shaft members 136. The shaft members 136 include a plurality of alternating spacers 138 and spheres 140 which are physically identical to and operate the same as spacers 31 and spheres 33 in the embodiment shown in FIGS. 1 through 5.

A tensioning member 142 is received through bores 144 and shaft members 136 which are located on a longitudinal axis of the shaft members 136. The tensioning member 142 is attached at a first end 146 thereof to an end shaft member 148 comprising a distal end of shaft 134, and the tensioning member is secured at the second end 149 thereof to a tensioning adjuster member 150. The tensioning adjuster member 150 comprises a knob 152 which includes a threaded shaft 154 thereon which shaft 154 is received within a threaded aperture 156 and handle 132. Upon rotation of the knob 152, the tension provided in tensioning member 142 can be adjusted as the tensioning adjuster 150 moves inwardly or outwardly in aperture 156.

A live attachment 158 is provided and is securely attached to end shaft member 148. In the embodiment shown in FIGS. 6 through 8, the live attachment 158 includes a movable member 160 which rotates about a longitudinal axis thereof.

An articulation member 162 is provided and extends through bores 164 in shaft members 136. The articulation member 162 in the present embodiment generally comprises a flexible drive shaft 166 which is attached at a first end 168 to the live attachment 158 and at a second end thereof 170 to a suitable rotational impetus means such as electric motor 174. As shown in FIG. 8, the drive shaft first end 168 engages a suitable gear mechanism 176 which in turn rotates the live attachment movable member 160. As shown in FIG. 8, the live attachment 158 comprises a chuck 178 and a bit 180. It is envisioned that other live attachments having a movable member thereof which rotates about an axis such as live attachment 158 can be provided including such movable members as a socket adapter for use with various sockets, and a screwdriver blade attachment.

A trigger mechanism 184 is provided to selectively engage the electric motor 174. A suitable electrical cord 186 is provided to connect the electrical motor 174 with a suitable power means.

In use, the device 130 as shown in FIGS. 6 through 8 allows the user thereof to perform necessary work operations which require a rotating work piecce in an area which is substantially inaccessible by the user. In doing so, the user would shape the shaft 134 into the desired shape necessary to allow the live attachment 158 to be in proper working position with the tensioning adjuster 150 being adjusted so as to decrease the tension in tensioning member 142 thereby allowing the individual shaft members 136 to be freely movable relative to each other. After the shaft 134 has been manipulated into the desired shape, the tension adjuster 150 is adjusted to increase the tension in the tensioning member 142 to a point where the shaft members 136 are rigidly retained in the desired shape. The tensioning adjuster 150 as shown in the second embodiment, performs the same function as the tightening lever 15 in the shaft device 1 as shown in the first embodiment of the present invention and is interchangeable therewith.

After the proper tension is applied to the shaft members 136, a user thereof can activate the desired live attachment 158 by operating the trigger mechanism 184. In doing so, the user can perform certain work functions which require rotation of a desired work piece when there are obstructions in the area of work which prohibit the user to perform the desired work without such an attachment.

It is to be understood that while certain forms of this invention have been illustrated and described herein, it is not to be limited to the specific forms or arrangement of parts described and shown.

What is claimed and desired to secure by Letters Patent is:

1. A locking flexible shaft device having a live attachment including:
   (a) an elongate flexible shaft having a plurality of points of articulation, a proximal end, a distal end, passageway means, and comprising a plurality of interengaging members;
      (i) said points of articulation being locations whereat said members interengage;
      (ii) said interengaging members being alternating spheroidal and cylindrical members;
   (b) tensioning means associated with said flexible shaft and extending through said passageway means and within said interengaging members;
      (i) said tensioning means being a tensioning wire extending between near said distal end of said flexible shaft and a tensioning means actuator;
      (ii) said tensioning wire having locked and unlocked orientations associated therewith such that when said tensioning means is in said unlocked orientation, then said interengaging members are easily manipulative relative to each other such that said shaft may be formed into a plurality of desired configurations; and, such that when said tensioning means is in said locked orientation, then said tensioning wire is stretched taut and said interengaging members are placed in frictional engagement with one another thereby locking said flexible shaft in a desired configuration;
      (iii) said tensioning means actuator being a lever mounted near said proximal end of said flexible shaft and being positionable between a first position, wherein said tensioning wire is slack, permitting said interengaging members to move with respect to one another, and a second position, wherein said interengaging members are biased into frictional engagement with one another, locking said flexible shaft into a selected configuration;
   (c) said live attachment connected to said distal end of said flexible shaft;
      (i) said live attachment having a rotatable member;
   (d) an attachment actuator located near said proximal end of said flexible shaft, remote from said live attachment and communicating with said live attachment by said actuator means;
      (i) said actuator means comprising a rotatable actuator wire extending through said passageway means and providing selective actuation of said attachment when direct access to said distal end is hindered;
      (ii) said rotatable wire extending between said attachment actuator and said live attachment; and
      (iii) said attachment actuator comprising selectively operable motor means including a rotating member communicating with said actuator wire whereby said actuator wire may be selectively rotated.

2. A locking flexible shaft having a live attachment including:
   (a) an elongate flexible shaft having a plurality of points of articulation, a proximal end, a distal end, passageway means, and comprising a plurality of interengaging members;
      (i) said points of articulation being locations whereat said members interengage;
      (ii) said interengaging members being alternating spheroidal and cylindrical members;
   (b) tensioning means associated with said flexible shaft and extending through said passageway means and within said interengaging members;
      (i) said tensioning means being a tensioning wire extending between near said distal end of said flexible shaft and a tensioning means actuator;
      (ii) said tensioning wire having locked and unlocked orientations associated therewith, such that, when said tensioning means is in said unlocked orientation, then said interengaging members are easily manipulative relative to each other such that said shaft may be formed into a plurality of desired configurations; and, such that, when said tensioning means is in said locked orientation, then said tensioning wire is stretched taut and said interengaging members are placed in frictional engagement with one another, thereby locking said flexible shaft in said desired configuration;
      (iii) said tensioning means actuator is attached to said tensioning means and comprises a screw-jack device in a mounting fixed relative to said shaft, said screw-jack device being selectively rotatable so as to motivate said screw-jack device back and forth along said flexible shaft, thereby selectively tightening or loosening said tensioning wire;
   (c) said live attachment connected to said distal end of said flexible shaft;
      (i) said live attachment having a rotatable member;
   (d) an attachment actuator located near said proximal end of said flexible shaft, remote from said live attachment and communicating with said live attachment by actuator means;
      (i) said actuator means comprising a rotatable actuator wire extending through said passageway means and providing selective actuation of said attachment when direct access to said distal end is hindered;
      (ii) said rotatable actuator wire extending between said attachment actuator and said live attachment; and
      (iii) said attachment actuator being motor means including a rotating member communicating with said actuator wire whereby said actuator wire may be selectively rotated.

3. A locking flexible shaft device having a live attachment including:
(a) an elongate flexible shaft having a plurality of points of articulation, a proximal end, a distal end, passageway means, and comprising a plurality of interengaging members;
  (i) said interengaging members being alternating spheroidal and cylindrical members;
  (ii) said points of articulation being locations whereat said members interengage; and said points of articulation being universal joints permitting articulation of limited angle in any direction;
(b) tensioning means associated with said flexible shaft and extending through said passageway means and generally within said interengaging members;
  (i) said tensioning means having locked and unlocked orientations associated therewith; said locked orientation producing frictional engagement between said interengaging members at said universal joints locking each universal joint in a preselected orientation thereby selectively locking said flexible shaft in an orientation selected from a plurality of orientations made possible by said plurality of universal joints; said unlocked orientation permitting free articulation about said universal joints;
(c) a tensioning means actuator associated with said tensioning means and being selectively manipulative to place said tensioning means in said locked and unlocked orientations thereof;
  (i) said tensioning means actuator being located near said proximal end of said flexible shaft;
  (ii) said tensioning means being a tensioning wire extending between near said distal end of said flexible shaft and near said tensioning means actuator;
(d) said live attachment being mounted near said distal end of said flexible shaft; and
(e) an attachment actuator located near said proximal end of said flexible shaft and remote from said live attachment and communicating with said live attachment;
(f) actuator means extending through said passageway means and, in combination with said attachment actuator, providing selective actuation of said attachment whereby an operator may selectively operate said live attachment by manipulation of said attachment actuator.

4. A locking flexible shaft device according to claim 3 wherein:
(a) said actuator means is an actuator wire extending between said attachment actuator and said live attachment;
(b) said live attachment includes a movable member and a stationary member;
  (i) said stationary member being rigidly secured to said distal end of said flexible shaft;
  (ii) said movable member being pivotally secured to said distal end of said flexible shaft;
(c) said attachment actuator comprises a trigger mechanism permitting said actuator wire to be selectively manipulated longitudinally along said shaft so as to operate said live attachment by selectively pivoting said movable member relative to, and into engagement with, said stationary member; and
(d) said actuator wire and said tensioning wire are adjacent one another and slidable with respect to one another such that said actuator wire may be manipulated when said tensioning means is in either said locked or said unlocked orientation thereof.

5. A locking flexible shaft device according to claim 4 wherein:
(a) said movable and stationary members comprise scissors blades and said live attachment is a pair of scissors.

6. A locking flexible shaft device according to claim 4 wherein:
(a) said movable and stationary members comprise clamp arms and said live attachment is a clamp.

7. A locking flexible shaft device having a live attachment including:
(a) an elongate flexible shaft having a plurality of points of articulation, a proximal end, a distal end, passageway means, and comprising a plurality of interengaging members;
  (i) said points of articulation being locations whereat said members interengage;
(b) tensioning means associated with said flexible shaft and extending through said passageway means and within said interengaging members;
  (i) said tensioning means being a tensioning wire extending between near said distal end of said flexible shaft and near said proximal end of said flexible shaft;
  (ii) said tensioning wire having locked and unlocked orientations associated therewith such that when said tensioning means is in said unlocked orientation, then said interengaging members are easily manipulative relative to each other such that said shaft may be formed into a plurality of desired configurations; and, such that when said tensioning means is in said locked orientation, then said tensioning wire is stretched taut and said interengaging members are placed in frictional engagement with one another thereby locking said flexible shaft in a desired configuration;
(c) a tensioning means actuator associated with said tensioning means and being selectively manipulative to place said tensioning means in said locked and unlocked orientations thereof; said tensioning means actuator being located near said proximal end of said flexible shaft;
  (i) said tensioning wire extending between said tensioning means actuator and near said distal end of said flexible shaft;
(d) said live attachment being connected to said distal end of said flexible shaft;
  (i) said live attachment having a rotatable member;
(e) an attachment actuator located near said proximal end of said flexible shaft, remote from said live attachment and communicating with said live attachment;
(f) actuator means comprising a rotatable actuator wire extending between said attachment actuator and said live attachment; and
(g) said attachment actuator comprising selectively operable motor means including a rotating member communicating with said actuator wire whereby said actuator wire may be selectively rotated.

* * * * *